United States Patent [19]

Simon et al.

[11] Patent Number: 5,017,190
[45] Date of Patent: May 21, 1991

[54] DOSAGE UNIT FOR DOSING A NUMBER OF MEASURED QUANTITIES OF A LIQUID, SUCH AS AN INSULIN PREPARATION, FROM A CONTAINER, PREFERABLY A CARTRIDGE

[75] Inventors: Bernd Simon, Wolfenbüttel, Fed. Rep. of Germany; Niels E. Holm, Birkerd; Fritz F. Bonnichsen, Lynge, both of Denmark

[73] Assignee: D.C.P. AF 1988 A/S, Vaerlose, Denmark

[21] Appl. No.: 411,506

[22] PCT Filed: Apr. 7, 1989

[86] PCT No.: PCT/DK88/00064
§ 371 Date: Oct. 5, 1989
§ 102(e) Date: Oct. 5, 1988

[87] PCT Pub. No.: WO88/07874
PCT Pub. Date: Oct. 20, 1988

[30] Foreign Application Priority Data

Apr. 7, 1987 [DK] Denmark .................... 1771/87

[51] Int. Cl.⁵ .............................................. A61M 5/00
[52] U.S. Cl. ................................. 604/207; 604/208; 604/209; 604/110
[58] Field of Search .............. 604/187, 207–411, 604/218–220, 110

[56] References Cited

U.S. PATENT DOCUMENTS

| | | | |
|---|---|---|---|
| 2,826,195 | 3/1958 | Ashkenaz | 604/201 |
| 4,246,898 | 1/1981 | Travalent et al. | 604/210 |
| 4,413,760 | 11/1983 | Paton | 604/209 |
| 4,444,335 | 4/1984 | Wood et al. | 604/208 |
| 4,475,905 | 10/1984 | Himmelstrup | 604/208 |
| 4,583,978 | 4/1986 | Porat et al. | 604/208 |
| 4,865,591 | 9/1989 | Sams | 604/208 |

FOREIGN PATENT DOCUMENTS 0058536 12/1982 European Pat. Off.
2311557 12/1976 France ...................... 604/208

Primary Examiner—Stephen C. Pellegrino
Assistant Examiner—Michael Rata
Attorney, Agent, or Firm—Willian Brinks Olds Hofer Gilson & Lione

[57] ABSTRACT

A dosage unit for dosing a number of measured quantities of a liquid, such as insulin, from a cartridge (2), said dosage unit comprising a cylindrical casing (1) for the cartridge (2), the distal end of the casing (1) being provided with means for fastening an injection needle (5) with two points protruding at opposite sides, one point (7) thereof being provided to be plunged into the cartridge (2). The other end of the casing comprises a piston rod (13) for exerting a force on a piston (8) inside the cartridge (2) and an adjustment means (20) provided with an inner thread (21), said adjustment means being in rotatable engagement with an outer thread (19) on the outside of the casing (1). The adjustment means (20) is adapted to limit the length of the stroke of the piston rod (13) after adjustment in accordance with a measuring scale (37, 38) stating the desired dosage quantity. This dosage unit enables an easy and precise adjustment of the desired quantity and ensures that the dosage unit cannot be used again inadvertently, when the cartridge is empty.

14 Claims, 3 Drawing Sheets

DOSAGE UNIT FOR DOSING A NUMBER OF MEASURED QUANTITIES OF A LIQUID, SUCH AS AN INSULIN PREPARATION, FROM A CONTAINER, PREFERABLY A CARTRIDGE

TECHNICAL FIELD

The invention relates to a dosage unit for dosing a number of measured quantities of a liquid, such as an insulin preparation, from a container, preferably a separate cartridge, said dosage unit comprising a cylindrical casing for the container, the distal end of the casing being provided with means for fastening a double-pointed injection needle, one point thereof being provided to pierce a membrane closing one end of the container, and said dosage unit comprising a piston rod for exerting a force on a piston closing the other end of the container, and an adjustment means provided with an internal thread, said adjustment means being in rotatable engagement with an external thread on the casing and adapted to adjust the length of the stroke of the piston rod according to the dosage needed in each case, the dosage being adjusted to be readable on a scale.

BACKGROUND ART

U.S. Pat. No. 4,475,905 discloses a dosage unit comprising a casing with an external thread over its entire length and a ring screwed on said thread. The ring is adjusted in relation to a measuring scale on the external surface of the casing, simultaneously serving as a retainer for a pin protruding through a slot of the casing, said pin being in solid connection with the piston of a syringe mounted in the casing.

U.S. Pat. No. 2,826,195 discloses a dosage unit for receiving a cartridge, the distal or front end of said cartridge being provided with a pierceable closure, through which one end of a double-pointed needle is pierced. After the cartridge has been inserted the needle is screwed to the distal end of the dosage unit one point passing through the adjacent closure of the cartridge.

Cartridges with different concentrations of insulin are used for the injection of insulin in dosage units of the above type. Usually, such cartridges contain 1.5 ml and the concentration of insulin herein can be 100 insulin units per ml, whereby the cartridge can contain 150 insulin units. In use a predetermined quantity is to be delivered by means of the dosage unit, preferably up to 40 insulin units per injection. By means of the dosage unit each cartridge can thus be used for several injections. Prior to each injection the dosage unit is adjusted to deliver exactly the amount of injectable preparation required in the particular case.

DISCLOSURE OF INVENTION

The present invention is characterised in that the dosage unit is provided with a first ratchet means between the casing and the piston rod, said ratchet means allowing the displacement of the piston rod in a direction towards the distal end of the casing and preventing the displacement in the opposite direction, and with a second ratchet means between the adjustment means and the casing or a second part of the dosage unit, which is unturnable in relation to the casing, and in relation to which the adjustment means is rotatable, said second ratchet means allowing the rotation of the adjustment means in a direction forward towards the distal end of the casing and preventing the rotation in the opposite direction.

Hereby it is ensured that the adjustment means and the piston remain in the positions they occupy subsequent to an injection until a new adjustment of the dose is performed. This is especially due to said ratchet means ensuring a stable locking of both the piston and the adjustment means in the position set up during premeditated use. Simultaneously the ratchet means prevent the piston rod and adjustment means from moving in a direction opposite to the desired one, the latter increasing the risk of a user either drawing air into the container or misjudging the amount of insulin remaining in the container.

According to the invention the first ratchet means is formed by circumferential, radial shoulders on the piston rod, each shoulder being bounded by conical surfaces tapering in a direction towards the front end of the piston rod, seen in the direction of movement during use, and where said shoulders and surfaces cooperate with a circumferential collar acting as a pawl, said collar being an integral part of the casing at the place, where the piston rod passes into the casing, and protruding forward towards the distal end of the casing. As a result the first ratchet means is easy to manufacture, and the manufacture of the corresponding parts is comparatively inexpensive.

In an advantageous embodiment of the invention the piston rod is provided with longitudinal grooves for radially inwardly protruding projections provided on the collar acting as a pawl on the casing, thus preventing the piston rod from rotating and consequently inadvertently altering the position of the rotatable adjustment means relative to the piston rod.

According to the invention the second ratchet means can also comprise a projection acting as a pawl, said projection being an integral part of the proximal end of the adjustment sleeve and cooperating with the longitudinal grooves of the piston rod. As a result the second ratchet means is also easy to manufacture, and the manufacture of the adjacent parts is comparatively inexpensive.

The inventive longitudinal grooves of the piston rod are of the same mutual angular distance. Thus the second ratchet means can be used during the adjustment of the desired dose, since each click of the second ratchet means which the user hears or feels corresponds to a predetermined quantity.

In a further embodiment of the invention the collar acting as a pawl is connected with the casing by means of a flange protruding radially inwards from the casing, said flange being of such a radial dimension that the proximal edge of the container in form of a cartridge is received herein, when the container is correctly positioned in the dosage unit. As a result it is possible to ensure that the collar acting as a pawl is retained with respect to the piston rod, as the adjacent edge of a container in form of a cartridge presses the collar against the piston rod provided the parts adjacent to the casing are suitably dimensioned.

Moreover, the inventive adjustment means can be in form of an oblong sleeve, being substantially of the same extension as the piston rod and the piston, and the external thread on the casing cooperating with the adjustment sleeve is placed adjacent to the proximal end of the casing and within an axial area ending at the front end of the piston of the container, when the dosage unit is ready for its first use. Thus the visible part of the casing is without a thread, and when made of transparent material it allows thus the user to control the contents of the container, for example with regard to air bubbles or remaining liquid, at any given moment. At the same time the adjustment means ensures that the travel of the piston rod is defined in a simple manner by the proximal end of the piston rod in relation to the adjacent end of the adjustment means.

The adjustment means being adjusted to the desired quantity, the displacement of the piston rod is defined in an especially stable and secure manner, if the proximal end of the piston rod is provided with a radially protruding head outside the adjustment means, said head being adapted to go into abutment with the adjacent end of the adjustment means, when the dosage quantity in question has been delivered.

The adjustment is further facilitated if, according to the invention, a circumferential measuring scale is provided at the proximal end of the adjustment means having an angular distance between the markings corresponding to the angular distance between the grooves in the piston rod, and a protective cap for the needle of the dosage unit is adapted to be fastened in a desired rotating position at the head of the piston rod during the use of the dosage unit, said cap carrying a marking to be set in front of the zero point of the measuring scale of the adjustment means. This enables the user to start from zero each time the dosage unit is to be adjusted.

Finally, the outside of the inventive piston rod has a longitudinal measuring scale for reading the number of dosage units delivered with each full turn of the adjustment means. Consequently the adjustment means is comparatively easily adjustable with visual control of the desired dose. The adjustment is preferably made before the injection needle is inserted into the injection site, and the visual control ensures that the user does not inject an overdose nor handle the dosage unit in a wrong way.

BRIEF DESCRIPTION OF DRAWINGS

The invention is described in greater detail below and with reference to the accompanying drawings, in which.

BEST MODE FOR CARRYING OUT THE INVENTION

Figure 1:
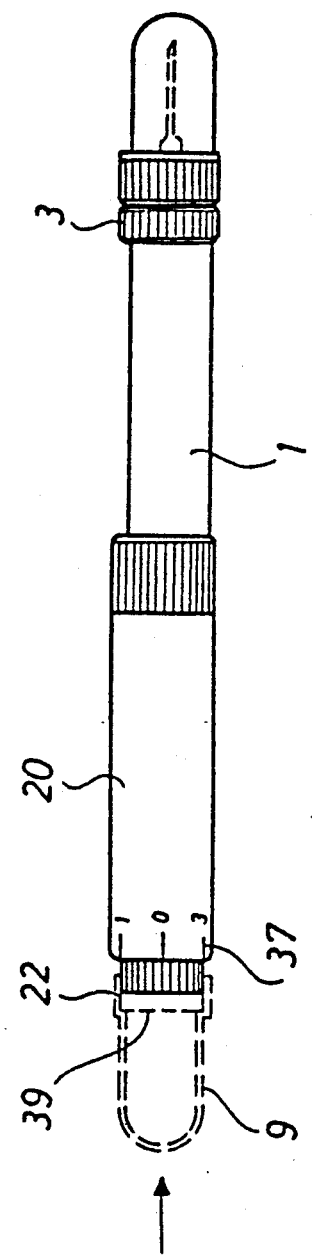
FIG. 1 is a side view of an inventive dosage unit.

The dosage unit illustrated in FIGS. 1-4 comprises a cylindrical casing 1 for an ordinary cartridge 2. One end of the casing is provided with a retaining cap 3 ensuring the retention of the cartridge 2 in the inside of the casing 1, after the cartridge has been inserted in the casing. The retaining cap 3 is fastened by a thread (not shown) or a snapping means. Optionally the retaining cap 3 is provided with barbs in engagement with a corresponding recess in the casing 1 thereby preventing the removal of the cartridge once the retaining cap has been fastened. The front of the retaining cap is provided with an opening 4 in its centre to receive a double-pointed needle 5. The needle 5 is mounted in a needle holder 6 which is screwed onto the retaining cap 3 by means of a cooperating thread. During its fastening the proximal end 7 of the needle pierces the pierceable closure 8 of the cartridge.

When the dosage unit is not in use, a protective cap 9 can be positioned on the outside part of the needle holder 6, said protective cap being retained by friction.

The proximal end of the casing 1 is formed with a circumfential, inwardly protruding flange 10 abutting the proximal end of the cartridge. Furthermore, there is provided a substantially axially extending, circumferential web 11 being an integral part of the inner periphery of the flange 10, said web 11 being slightly tilted in a direction inside towards the centre of the opening of the casing, when the cartridge is in position. This tilt can partially be ensured by means of an inner, circumferential bead usually extending along the edge of the cartridge 2, and partially by means of an outer, circumferential enlargement 12 of the web 11.

A piston rod 13 is received in the opening of the casing 1 limited by the flange 10 with the web 11, said piston rod being provided with a number of radial shoulders, e.g. 14 and 15, of the same mutual distance. A conical surface 16 extends between each two shoulders, said surface tapering in a direction towards the proximal end of the piston rod 13. The radial shoulders and the conical surfaces on the piston rod 13 are adapted to cooperate with the web 11 at the opening of the casing 1 in such a way that the web 11 acts as a pawl in the first ratchet means with the general reference numeral 17.

The ratchet means 17 ensures that the piston rod 13 is only subjected to a forward movement towards the front end of the casing 1. This forward movement progresses stepwise, each step being of the same length. The piston rod 13 is adapted to exert a force on a piston 18 inside the cartridge 2, said piston pressing the contents of the cartridge out through the needle 5 when it is displaced by means of the piston rod.

The proximal end of the piston rod 13 has as an integral part a head 22 limited by two radial surfaces and a circumferential surface 23, the latter having a larger radius than the remaining part of the piston rod 13. The circumferential surface 23 is of the same dimension as the inner side of the protective cap 9, so that the latter can be placed on the head 22 of the piston rod 13 during the use of the dosage unit, the protective cap being held in place by friction. The peripheral surface of the head 22 can optionally be provided with axial grooves 24 cooperating with corresponding projections (not shown) in the protective cap 9 in such a way that the cap 9 can be placed on the head 22 in any desired rotating position.

Directly adjacent the proximal end of the casing and along a distance approximately ending at the place corresponding to the position of the front end of the piston 18 before its first movement, there is an external thread 19. A sleeve-shaped adjustment means 20 with a corresponding internal thread 21 is along its entire length received on said external thread 19.

This sleeve-shaped adjustment means 20 has a length substantially corresponding to the axial length of the piston 18 plus the length of the section of the piston rod 13 carrying the shoulders 14, 15 and the conical surfaces 16 situated therebetween.

More precisely the sleeve-shaped adjustment means is of such a length that when its front or distal end in its starting position is approximately opposite the distal end of the piston 18, its proximal end abuts the radial surface of the head 22 of the piston rod 13 facing towards the distal end of the dosage unit. At this place the adjustment means 20 has a circumferential, radial and inwardly directed flange 24, the inner periphery of which is adjacent to the outer periphery of the piston rod, cf. FIG. 3. Furthermore, the flange 24 on the adjustment means 20 is provided with a projection 25 radially protruding inside the periphery of the flange. The projection 25 forms an integral part with the flange 24 and is defined by suitable recesses 26 and 27. These recesses enable the projection 25 to be pressed radially outwardly in relation to the flange 24, cf. FIG. 3. Further, the projection 25 is positioned at an angle with respect to the radius at the place in question on the flange 24, and is adapted to be in engagement with longitudinal grooves 28, 29, 30 and 31 in the piston rod 13, cf. FIG. 3. The longitudinal grooves 28, 29, 30 and 31 are of the same mutual angular distance (i.e., spaced at equal distances from one another around an outside surface of the piston rod 13) and cooperate with the projection 25 on the flange 24 in such a way that they form a second ratchet means having the general reference numeral 32. This ratchet means ensures that the adjustment sleeve 20 is only rotatable in a clockwise direction in relation to the piston rod 13, when seen in FIG. 3.

Figure 2A:
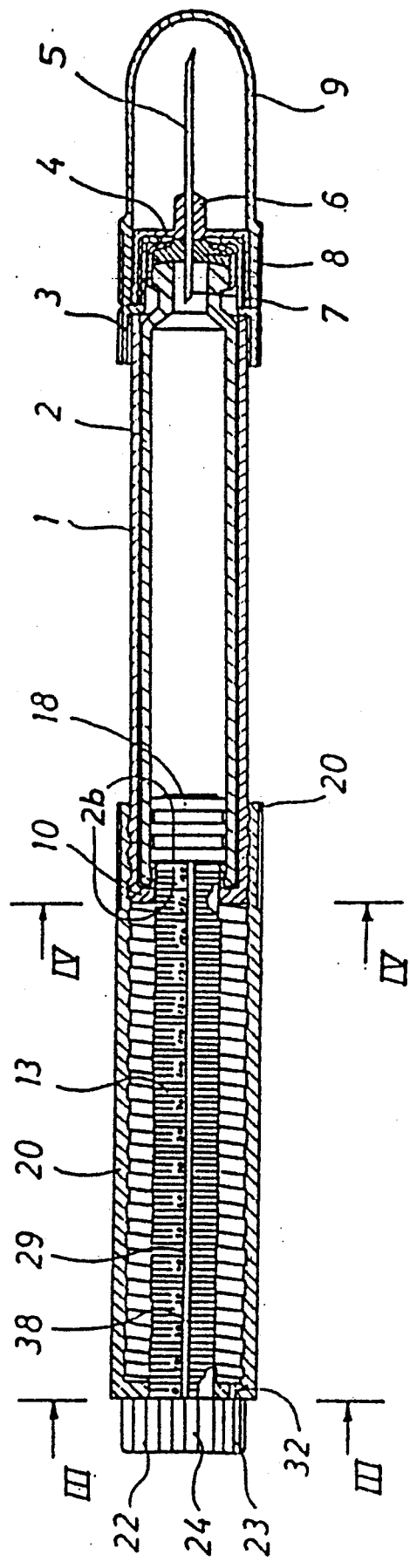
FIG. 2a is an enlarged sectional view of the dosage unit of FIG. 1.
Figure 2B:
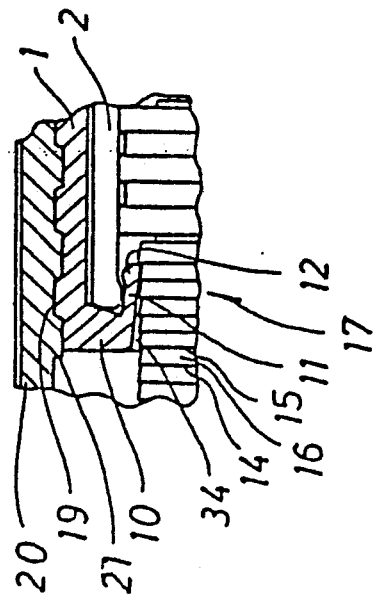
FIG. 2b is a further enlarged sectional view of the circled singled part shown in FIG. 2a, FIG. 3 is a sectional view along the line III—III of FIG. 2.
Figure 4:
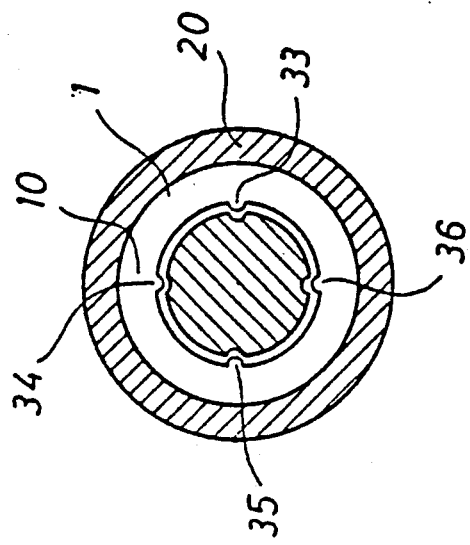
FIG. 4 is a sectional view along the line IV—IV of FIG. 2.
Figure 3:
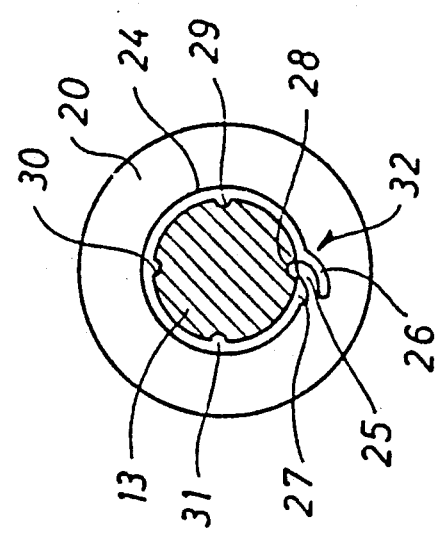

The longitudinal grooves 28, 29, 30 and 31 in the piston rod extend along the entire length of the narrow part of the piston rod, cf. FIGS. 2a and 2b. At the same time the grooves 28, 29, 30 and 31 cooperate with corresponding projections 33, 34, 35 and 36, cf. FIG. 4, said projections being provided at the inside of the web 11 at the entrance to the casing 1. This ensures the retention of the piston rod in relation to the adjustment means 20 during the rotation of the latter.

As illustrated in FIG. 1, the proximal end of the adjustment means is provided with a circumferential measuring scale 37, and the piston rod 13 is provided with a longitudinal measuring scale 38, cf. FIGS. 2a and 2b. The circumferential measuring scale 37 is adapted to the individual steps of the second ratchet means 32, and the longitudinal measuring scale 38 is adapted to the number of full turns of the adjustment means 20. The two measuring scales 37 and 38 are provided with markings stating the number of units to be dosed when adjusting the dosage unit. For use during adjustment the protective cap 9 is advantageously provided with a longitudinal line on its outer surface (not shown) adjacent to the mouth. This line is positioned in front of the zero point on the circumferential measuring scale 37, when the dosage unit is being used and the protective cap 9 is placed on the head 22 of the piston rod 13, as indicated with dotted lines in FIG. 1. Then the user rotates the adjustment means and either the number of clicks is counted or the desired number of dosage units is read by using the two measuring scales 37 and 38. Each turn of the adjustment means corresponds to a predetermined number of insulin units to be delivered during the subsequent pressing of the piston rod, said number being read from the circumferential measuring scale 37. The number of turns and the resulting number of insulin units to be injected is read from the longitudinal measuring scale 38. When the adjustment means 20 is adjusted in relation to the longitudinal measuring scale 38 and the circumferential measuring scale 37, the needle of the dosage unit is positioned on the desired site of injection and inserted. The head 22 of the piston rod 13 is then pressed until it again abuts the adjustment means 20. The pressing of the head 22 of the piston rod 13 is suitably performed via the protective cap 9, if said cap is provided with an inner abutment shoulder 39 to abut the head 22, cf. FIG. 1. After use and withdrawal of the dosage unit the protective cap 9 is placed over the needle 5, until a new injection has to be performed and the above procedure is repeated.

The various parts of the dosage unit are manufactured of plastics and the casing 1 is made of a transparent plastic material, so that the user is able to see at any given moment how much insulin is left in the cartridge 2. The cartridge used is preferably a cartridge sold under the name Penfill ® by NOVO Industri A/S.

The present invention is described in its preferred embodiment. Many alterations can, however, be made without deviation from the scope of the invention. The second ratchet means can, for example, be situated between the adjustment means 20 and the end of the casing 1, where the part acting as a pawl is situated on the casing and cooperates with grooves in the internal thread 21 of the adjustment means 20. The mutual distance between the radial shoulders 14 and 15 on the piston rod 13 is suitably adapted to the units of the longitudinal measuring scale 38 so that the displacement of the piston rod between two clicks corresponds to a full turn of the adjustment means 20. Thus the user is also able to detect audibly when the desired quantity is adjusted.

The above dosage unit is a disposable one, since it is impossible to remove the empty cartridge, thus ensuring that other persons are unable to inadvertently use the dosage unit when it has been disposed of by the original user.

If desired, the dosage unit can also be provided with a first ratchet means 17, which stops to function when the cartridge is emptied and optionally taken out, so that the individual parts of the dosage unit can be returned to their respective starting positions ready to receive a new cartridge.

The ratchet means in question can optionally also be formed in such a way that the user can overcome the movementimpeding function of the ratchet means when stronger force is intentionally exerted.

Finally, instead of a separate cartridge acting as a container for the liquid in question, a container forming an integral part of the casing can also be used.

We claim:

1. A dosage unit for dosing a number of measured quantities of a liquid, such as an insulin preparation, from a container, preferably a separate cartridge, said dosage unit comprising a cylindrical casing for the container, the distal end of the casing being provided with means for fastening a double-pointed injection needle, one point thereof being provided to pierce a membrane closing one end of the container, and said dosage unit comprising a piston rod for exerting a force on a piston closing the other end of the container, and an adjustment means provided with an internal thread, said adjustment means being in rotatable engagement with an external thread on the casing and adapted to adjust the length of the stroke of the piston rod according to the dosage needed in each case, the dosage being adjusted to be readable on a scale located on the dosage unit, characterised in that the dosage unit is provided with a first ratchet means (17) between the casing (1) and the piston rod (13), said ratchet means allowing the displacement of the piston rod (13) in a direction towards the distal end of the casing and preventing the displacement in the opposite direction, and with a second ratchet means (32) between the adjustment means (20) and the casing (1) or a second part of the dosage unit, which is unturnable in relation to the casing, and in relation to which the adjustment means is rotatable, said second ratchet means allowing the rotation of the adjustment means (20) in a direction forward towards the distal end of the casing (1) and preventing the rotation in the opposite direction.

2. A dosage unit as claimed in claim 1, characterised in that the first ratchet means (17) is formed by circumferential, radial shoulders (14, 15) on the piston rod (13), each shoulder being bounded by conical surfaces (16) tapering in a direction towards the front end of the piston rod (13), seen in the direction of movement during use, and where said shoulders (14, 15) and surfaces (16) cooperate with a circumferential collar acting as a pawl (11), said collar being an integral part of the casing (1) at the place, where the piston rod (13) passes into the casing, and protruding forward towards the distal end of the casing.

3. A dosage unit as claimed in claim 2, characterised in that the piston rod (13) is provided with longitudinal grooves (28, 29, 30 and 31) for radially inwardly protruding projections (33, 34, 35 and 36) provided on the collar acting as a pawl (11) on the casing (1).

4. A dosage unit as claimed in claim 3, characterised in that the second ratchet means (32) comprises a projection (25) acting as a pawl, said projection being an integral part of the proximal end of the adjustment sleeve (20) and capable of engaging the longitudinal grooves (28, 29, 30 and 31) of the piston rod (13).

5. A dosage unit as claimed in claim 4, characterised in that the longitudinal grooves (28, 29, 30 and 31) of the piston rod (13) are spaced at equal distances from one another around an outside surface of the piston rod (13).

6. A dosage unit as claimed in claim 2 or 3, characterised in that the collar acting as a pawl (11) is connected with the casing (1) by means of a flange protruding radially inwards from the casing, said flange being of such a radial dimension that the proximal edge of the container in form of a cartridge (2) is received herein, when the container is correctly positioned in the dosage unit.

7. A dosage unit as claimed in claim 1, 2, 3, 4, or 5 characterised in that the adjustment means (20) is in form of an oblong sleeve being substantially of the same extension as the piston rod (13) and the piston (8), and the external thread (19) on the casing (1) cooperating with the adjustment sleeve is placed adjacent to the proximal end of the casing (1) and within an axial area ending at the front end of the piston of the container, when the dosage unit is ready for its first use.

8. A dosage unit as claimed in claim 6, characterised in that the adjustment means (20) is in the form of an oblong sleeve being substantially of the same extension as the piston rod (13) and the piston (8), and the external thread (19) on the casing (1) cooperating with the adjustment sleeve is placed adjacent to the proximal end of the casing (1) and within an axial area ending at the front end of the piston of the container, when the dosage unit is ready for its first use.

9. A dosage unit as claimed in claim 6, characterised in that the piston rod has a longitudinal measuring scale (38) on its outside for reading the number of dosage units delivered with each full turn of the adjustment means (20).

10. A dosage unit as claimed in claim 7, characterised in that the piston rod has a longitudinal measuring scale (38) on its outside for reading the number of dosage units delivered with each full turn of the adjustment means (20).

11. A dosage unit as claimed in claim 7, characterised in that the proximal end of the piston rod is provided with a radially protruding head (22) outside the adjustment means (20), said head being adapted to go into abutment with the adjacent end of the adjustment means, when the dosage quantity in question has been delivered.

12. A dosage unit as claimed in claim 11, characterised in that a circumferential measuring scale (37) is provided at the proximal end of the adjustment means (20) and having an angular distance between the markings corresponding to the angular distance between the grooves in the piston rod, and a protective cap (9) for the needle (5) of the dosage unit is adapted to be fastened in a desired rotating position at the head (22) of the piston rod (13) during the use of the dosage unit, said cap carrying a marking to be set in front of the zero point of the measuring scale (37) of the adjustment means (20).

13. A dosage unit as claimed in claim 5, 11 or 12, characterised in that the piston rod has a longitudinal measuring scale (38) on its outside for reading the number of dosage units delivered with each full turn of the adjustment means (20).

14. A dosage unit for dosing a number of measured quantities of a liquid, such as an insulin preparation, from a container, preferably a separate cartridge, said dosage unit comprising a cylindrical casing for the container, the distal end of the casing being provided with means for fastening a double-pointed injection needle, one point thereof being provided to pierce a membrane closing one end of the container, and said dosage unit comprising a piston rod for exerting a force on a piston closing the other end of the container, and an adjustment means provided with an internal thread, said adjustment means being in rotatable engagement with an external thread on the casing and adapted to adjust the length of the stroke of the piston rod according to the dosage needed in each case, the dosage being adjusted to be readable on a scale located on the dosage unit, characterised in that the dosage unit is provided with a first ratchet means (17) between the casing (1) and the piston rod (13), said ratchet means allowing the displacement of the piston rod (13) in a direction towards the distal end of the casing and preventing the displacement in the opposite direction, and with a second ratchet means (32) between the adjustment means (20) and the casing (1) or a second part of the dosage unit, which is unturnable in relation to the casing, and in relation to which the adjustment means is rotatable, said second ratchet means allowing the rotation of the adjustment means (20) in a direction forward towards the distal end of the casing (1) and preventing the rotation in the opposite direction, the ratchet means (17, 32) being adapted in such a way that the effect of the movement-impeding parts can temporarily be overcome by exerting a stronger force.

* * * * *